United States Patent [19]

Nelson

[11] 4,188,473
[45] Feb. 12, 1980

[54] HIGH TEMPERATURE POLYMERS

[75] Inventor: Donald L. Nelson, Lake Jackson, Tex.

[73] Assignee: The Dow Chemical Company, Midland, Mich.

[21] Appl. No.: 869,337

[22] Filed: Jan. 13, 1978

Related U.S. Application Data

[63] Continuation-in-part of Ser. No. 394,011, Sep. 4, 1973, abandoned.

[51] Int. Cl.$^2$ .............................................. C08G 65/00
[52] U.S. Cl. ..................................... 528/86; 528/141; 528/143; 528/265; 528/373
[58] Field of Search ............... 260/47 R, 52; 528/143, 528/86, 265, 373

[56] References Cited

U.S. PATENT DOCUMENTS

| | | | |
|---|---|---|---|
| 3,274,157 | 9/1966 | Doedens | 260/47 |
| 3,323,962 | 6/1967 | Sprengling et al. | 156/184 |
| 3,405,091 | 10/1968 | Sprengling et al. | 260/47 |

FOREIGN PATENT DOCUMENTS 1021935  3/1966  United Kingdom.
 377318  5/1973  U.S.S.R..

OTHER PUBLICATIONS

Nishizaki et al., "Thermosetting Resin Compositions," Chemical Abstracts 74, 13748c (1971).
Aulova et al., "Thermosetting Polymers," Chemical Abstracts 79, 54430q (1973).
Khadzhistoyanova et al., "Oligomeric Products from Diphenyl Ether," Chemical Abstracts 81, 136824b (1974).

Primary Examiner—Earl A. Nielsen
Attorney, Agent, or Firm—G. R. Baker

[57] ABSTRACT

Polymeric materials and their thermoset, resinous products prepared by the polymerization of a mixture containing at least two different monomeric structures selected from the group having the general formula

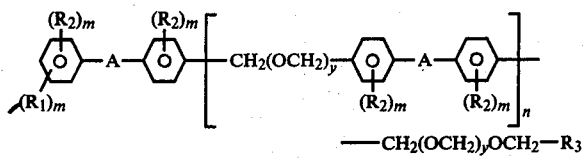

wherein each A represents a chalcogen independently selected from the group oxygen and sulfur; $R_1$ represents a member selected from the group hydrogen, —$CH_2(OCH_2)_yOCH_2$—$R_3$; each $R_2$ represents a member independently selected from the group consisting of $R_1$, halogen and an alkyl group of 1 to 10 carbon atoms; $R_3$ represents a member selected from the group consisting of H, methyl, ethyl and propyl; each m represents an independently selected integer from 1 to 2; n represents an integer from 0 to 60 and y represents an integer from 0 to 3 in the presence of an acid catalyst at a temperature of from between about 140° and about 165° C. for from several minutes to several hours. The thermoset resinous products are obtained by further heating the aforedescribed polymeric materials at a temperature of from about 170° C. to about 260° C. for from several minutes to several hours.

The polymeric materials are low melting solids which are useful as laminating, molding, film-forming materials which can be cured or thermoset by heat.

12 Claims, No Drawings

HIGH TEMPERATURE POLYMERS

CROSS-REFERENCE TO RELATED APPLICATIONS

This application is a continuation-in-part of our prior filed application Serial No. 394,011, filed by us Sept. 4, 1973, now abandoned, entitled HIGH TEMPERATURE POLYMERS.

BACKGROUND OF THE INVENTION

Organic condensation products derived from halomethylated diaromatic ethers as well as from poly(methylol diaromatic ethers) to produce poly(methylene diaromatic ethers) are described in several U.S. patents, namely, U.S. Pat. Nos. 2,911,380, 3,004,072, 3,000,839, 3,269,973 and 3,342,873. The polymers prepared in accordance with these patents have good thermal stability and are useful in molding, potting and film forming. The techniques described in the literature, including the patent literature above set forth, have suffered from the by-product halogen acid produced at one stage or another. The production of the halogen acid creates a handling problem during manufacture as well as the difficulty in removing the traces of the acid from the final product.

Another difficulty with the prior art technique is that the monomers are not readily formed into prepolymers which are more economical to employ as well as more precise in applications such as molding and potting.

BRIEF DESCRIPTION OF THE INVENTION

In accordance with the present invention, at least two different compounds selected from the group consisting of

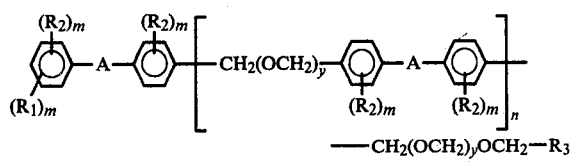
——$CH_2(OCH_2)_yOCH_2$—$R_3$ wherein each A represents a chalcogen independently selected from the group oxygen and sulfur; $R_1$ represents a member selected from the group hydrogen, —$CH_2(OCH_2)_yOCH_2$-$R_3$; each $R_2$ represents a member independently selected from the group consisting of $R_1$, halogen and an alkyl group of 1 to 10 carbon atoms; $R_3$ represents a member selected from the group consisting of H, methyl, ethyl and propyl; each m represents an independently selected integer from 1 to 2; n represents an integer from 0 to 60 and y represents an integer from 0 to 3 are condensed in the presence of an acid catalyst at a temperature of from about 140° and about 165° C. for from several minutes to several hours. Temperatures above about 165° C. may be employed but are not recommended as the reaction is difficult to control and the products are not uniformly reproducible. The product of this reaction is usable as is, being a solid thermoplastic resinous material, although it is more useful when it is further cured into a thermoset polymer by heating at from about 170° C. to about 260° C. for from several minutes to several hours. Good results have been obtained when a mixture of (1) diphenyl oxide,
(2) methoxy methyl and dimethoxy methyl diphenyl oxide,
(3) methoxy poly(methoxy)methyl and di[(methoxy) poly(methoxy)methyl] diphenyl oxide, and
(4) methoxy methyl poly(phenoxyphenyl methylene) phenoxybenzene which mixture may contain bis(phenoxyphenyl)methane, is heated to 140° to 165° C. for 1 to 2 hours in admixture with about 0.2 to 0.3 weight percent of a Friedel-Crafts acid catalyst and particularly the alkylated diphenyl oxide disulfonic acids.

The reaction compounds can be prepared individually but are more economically prepared in admixture according to the following process.

A formaldehyde-diaromatic ether reaction product is a mixture of monomers each having the formula

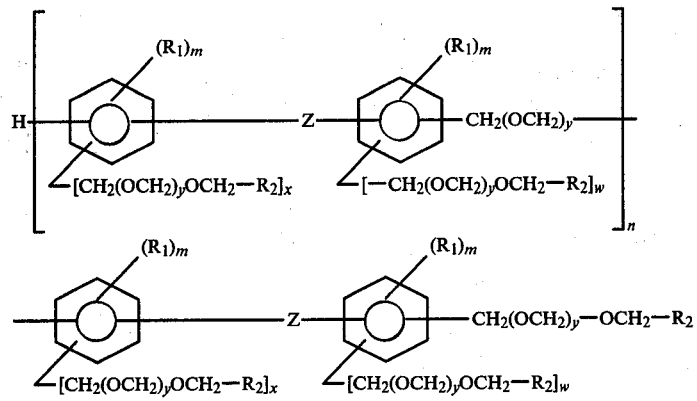

wherein $R_1$ is independently hydrogen, an alkyl group of 1 to 10 carbon atoms, or halogen, $R_2$ is selected from hydrogen, methyl, ethyl or propyl, Z is selected from oxygen, sulfur or mixtures thereof, n is 0–9, m is 0–2, y is 0–3, x, w are 0 or 1, the sum of w and x has an average value of from 0.1 to 1.0 with the proviso that when n is 0, y is at least 1.

The process for making the starting materials useful in the present invention comprises preparing a liquid formaldehyde-diaromatic ether product by heating to a temperature in the range from about 50° to about 250° C. a mixture of (a) a diaryl compound selected from diphenyl oxide, diphenyl sulfide, their alkylated derivatives, their halogenated derivatives or mixtures thereof,
(b) formaldehyde,
(c) water, and
(d) an aliphatic hydroxy hydrocarbon compound, in the presence of a catalytic amount of a strong acid catalyst wherein the amount of formaldehyde used ranges from about 1 to about 3 moles per mole of diaryl compound, the amount of water ranges from about 0.01 to about 2 moles per mole of diaryl compound and the amount of hydroxy hydrocarbon compound ranges from about 0.3 to about 10 moles per mole of diaryl compound.

The reaction products are useful in that they can be heated with strong acids and cross-linked to encapsulate electrical components, the reaction products are useful per se as nontoxic dielectric fluids for transformers and the like.

DETAILED DESCRIPTION OF THE INVENTION

The diaromatic ethers or diaryl ethers which can be reacted with formaldehyde to prepare the reaction products of this invention are diphenyl ether (diphenyl oxide) and diphenyl sulfide. Reaction products can also be prepared from the alkylated derivatives of the foregoing wherein one or both aromatic rings are substituted by one or two alkyl groups of 1 to 10 carbon atoms each.

If desired, the diaromatic ethers can be halogenated in one or both rings with fluorine, chlorine, bromine, or iodine groups. Mixtures of the foregoing are also useful in this invention.

The above diaromatic ethers are mixed and reacted with about 1 to about 3 moles of formaldehyde at a temperature range from about 50° to about 250° C. in the presence of about 0.01 to about 2 moles of water per mole of diaryl ether and in the presence of about 0.03 to about 10 moles of an aliphatic hydroxy hydrocarbon compound having 0 to 4 ether oxygens and at least one free hydroxyl group.

The presence of water in the ranges recited above is essential to this invention since the use of amounts below this range results in very low yields of the desired reaction product while amounts greater than this amount result in greatly increased reaction times.

The above reaction proceeds readily in the presence of a catalytic amount of a strong acid catalyst. For the purposes of this invention, a catalytic amount is defined as about 1 to about 20 mol percent of the strong acid based on the diaryl ether.

Examples of strong acid catalysts are sulfuric, phosphoric, p-toluene sulfonic acid, perchloric, alkylated diphenyl oxide disulfonic acid, and the like.

A commercial mixture of formaldehyde, methanol and water sold under the trade name Methyl Formcel ® is a convenient source of the above formaldehyde reactant.

Examples of the above aliphatic hydroxy hydrocarbon compounds are: monohydric alcohols of 1 to 12 carbons such as methanol, ethanol, propanol, butanol, 2-ethyl hexanol, and the like; glycols of 2 to 4 carbons such as ethylene glycol, 1,3-propylene glycol, 1,2-propylene glycol and butane 1,4-diol; polyglycols of 4 to 12 carbons such as diethylene glycol, triethylene glycol, dipropylene glycol, tripropylene glycol, dipropylene glycol, tripropylene glycol, and the like; monoalkyl ethers of glycols of 3 to 12 carbons such as ethylene glycol monomethyl ether, ethylene glycol monoethyl ether, 1,2-propylene glycol monomethyl ether, ethylene glycol monobutyl ether, and the like; and monoalkylethers of polyglycols of 5 to 12 carbons such as diethylene glycol monomethyl ether, diethylene glycol monoethyl ether, diethylene glycol monobutyl ether, and the like.

The following examples are presented to illustrate but not limit the invention.

Preparation A

One thousand grams (5.56 moles) of diphenyl oxide was charged to a 2 liter stainless steel bomb along with 180 grams (5.6 moles) of methanol, 180 grams (5.6 moles) of 92% paraformaldehyde, 100 grams of water and 175 grams (17.5% by weight based on the diphenyl oxide) of Dowex 50, H+form brand ion exchange resin. The bomb was fitted with a stirrer, closed, heated to 145° C. and maintained thereat for 4.5 hours. The final pressure of the bomb was 175 psig. The bomb was cooled, opened, and the liquid was transferred to a separatory funnel. One hundred milliliters of water and 200 ml. methylene chloride were added with stirring. The liquid in the funnel was permitted to settle and the organic layer which formed separated from the aqueous layer. The separated organic layer was washed with a 10% aqueous NaOH solution and finally with distilled water. Thereafter, the washed organic layer was subjected to distillation to remove the water, residual methylene chloride and unreacted diphenyl oxide. Seven hundred twelve grams of diphenyl oxide were recovered. The distillation was continued to a pot temperature of 225° C. The head temperature varied from 165° C. (5-½ mm. Hg) to 197 (4 mm. Hg). As a result of these operations, there was obtained 254 grams of product which, upon analysis by nuclear magnetic resonance and vapor phase chromatography, was found to have an average structure of approximately

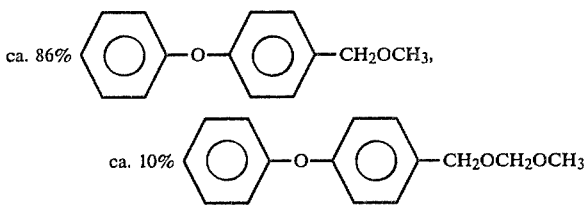

and about 4% di(methoxy methyl)diphenyl oxide and an average equivalent weight of 214.

Preparation B

In the manner of Preparation A above, 27.2 kg. (0.16 kg. moles) of diphenyl oxide was reacted with 17.44 kg. (0.32 kg. mole) of 55% formaldehyde and 1.6 kg. (0.016 kg. mole) of sulfuric acid to obtain a product having an average molecular weight of about 700.

Preparation C

In the manner of Preparation A, 34 pounds of diphenyl oxide was reacted with 6.8 pounds of paraformaldehyde, 13.17 pounds of methanol, 3.70 pounds of water and 4.11 pounds of sulfuric acid to obtain a product having an average equivalent weight of about 262.

The following examples illustrate the use of various monomeric mixtures prepared above in the process of the present invention.

EXAMPLE 1

An acid resistant vessel equipped with a stirrer, thermowell, Dean Stark trap and a condenser was charged with 82.5 grams of the liquid system hereafter called MFDPO prepared in the manner of Preparation A and having an average equivalent weight of 214 and 0.24 grams of dodecyl diphenyl oxide disulfonic acid. The products were stirred for approximately 3 hours at 150° C. and approximately 1-½ hours at 170° C. Polymer distillate measured 13.4 ml. A cold flow solid resulted and put into a 60% solids solution with a 50/50 mix of toluene and benzene. The product had a viscosity of 168 centipoise at 26° C. A thin, tough, temperature stable film, resulted after curing in a cycle of 25° to 250° C. over a 6 hour period. The product lost 4.6 percent of its base weight after 500 hours exposure to 500° F.

EXAMPLE 2

An acid resistant vessel equipped with a stirrer, thermowell, Dean Stark trap and condenser was charged with 300 grams of MFDPO prepolymer with an average molecular weight of 700 obtained from Preparation B and 3 grams of p-toluene sulfonic acid dissolved in 5 grams of methanol. The ingredients were stirred for 1 hour and 45 minutes at 150° C. Polymer distillate measured 14.4 ml. Major constituents of the distillate were methanol, formaldehyde and water. Methylal and diphenyl oxide were found as minor components. A cold flow solid resulted and was dissolved at a 60% solids level in a 50/50 mix of toluene and benzene. The product had a stroke cure gel time of 35 seconds at 150° C. The solution viscosity was 642 centipoise at 26° C. A tough, temperature stable film resulted after curing with a cycle of 77° F. to 500° F. over a 14 hour period. The film lost 8.1% of its base weight after 1024 hours exposure to 500° F.

EXAMPLE 3

An acid resistant vessel equipped as in the above examples was charged with 400 grams of MFDPO prepolymer with an average molecular weight of 700 (Preparation B) and 1.2 grams (0.3% based on MFDPO) of dodecyl diphenyl oxide disulfonic acid. The products were stirred for approximately 1 hour and 45 minutes at 150° C. Polymer distillate measured 21.9 ml. The polymer exhibited an average molecular weight of 10,000–11,000. The viscosity at 26° C. was 66 centipoise. Using a cure cycle of 14 hours from 77° to 500° F., the weight loss of a thin film was 8.2% after 1024 hours exposure to 500° F.

EXAMPLE 4

An acid resistant vessel equipped as in the above examples was charged with 200 grams of MFDPO prepolymer with an average molecular weight of 700 (Preparation B) and 2.0 grams (1.0% based on MFDPO) of dodecyl diphenyl oxide disulfonic acid. The temperature was set at 150° C. and the heating cycle began. A violent uncontrollable reaction occurred, yielding a gelled foam. 11.85 Ml. of polymer distillate resulted.

EXAMPLE 5

An acid resistant vessel equipped as in the above examples was charged with 150 grams of MFDPO prepolymer with an average equivalent weight of 262 obtained by distillation of a product prepared in the manner of Preparation C, and 0.6 grams (0.4% based on MFDPO) of dodecyl diphenyl oxide disulfonic acid. The products were stirred for 2 hours and 45 minutes at 150° C. Polymer distillate measured 17.5 ml. The resultant resin had a gel time of 6.4 minutes at 167° C.

The following examples illustrate the effect of various acids and curing cycles employing the monomers in accordance with the present invention.

TABLE 1

Polymerization of Type 1 Intermediate*

| | Catalyst | | |
|---|---|---|---|
| | p-Tol. Sulf.[3] Acid | p-Tol. Sulf. Acid | DDODA[4] |
| Concentration Used | 1.0% | 0.75% | 0.3% |
| Reaction Time 150° C. | 1 hr. 45 min. | 2.0 hrs. | 1 hr. 45 min. |
| Theor. Distillate[1] | 45.8% | 37.5% | 48.5% |
| Appearance | Cloudy | Cloudy | Cloudy |
| Viscosity[2] at 26° C. | 642 cps. | 73 cps. | 66 cps. |

*Prepolymer with an average molecular weight of 700 or greater as employed in Examples 2, 3 and 4.
[1]Theoretical distillate, calculated as methanol, is used to monitor the degree of polymerization. The Type I prepolymer will gel at 60% theoretical distillate.
[2]60% solids in a 50/50 blend of toluene and benzene.
[3]p-Toluene sulfonic acid.
[4]Dodecyl diphenyl oxide disulfonic acid.

TABLE 2

Polymerization of Type 2 Intermediate*

| | p-Tol. Sulf.[5] Acid | DDODA[6] |
|---|---|---|
| Concentration Used | 1.0% | 0.3% |
| Reaction Time | 4.0 hrs.[1] | 4 hrs. 20 min.[2] |
| Theor. Distillate[3] | 80.5% | 87.0% |
| Appearance | Cloudy | Clear |
| Viscosity at 26° C.[4] | 544 cps. | 168 cps. |

*A mixture of predominantly monofunctional formaldehyde-diaromatic ethers as employed in Example 1.
[1]150° C.
[2]150° C. except last hour run at 170° C.
[3]Gel point was not defined.
[4]60% solids in a 50/50 blend of toluene and benzene.
[5]p-Toluene sulfonic acid.
[6]Dodecyl diphenyl oxide disulfonic acid.

The following examples illustrate the effect of intermediate selection on temperature stability (Table 3), effect of cure cycle (Table 4), and effect of catalyst selection (Table 5).

TABLE 3

Effect of Intermediate Selection on Temperature Stability

| | | % Wt. Loss After 500 Hrs. at 500° F. | |
|---|---|---|---|
| Catalyst | Cure Cycle[1] | Type I[2] | Type II[3] |
| p-Tol.[4] | 6 hrs. | 5.36 | 3.99 |
| DDODA[5] | 6 hrs. | 5.74 | 4.63 |
| p-Tol. | 14 hrs. | 3.14 | 2.29 |
| DDODA | 14 hrs. | 3.54 | 3.36 |

[1]6 Hour Cycle
5 hrs. from 25° C. to 170° C.
15 min. to 250° C.
1 hr. bake at 250° C.
14 Hour Cycle
13 hrs. from 25° C. to 205° C.
1 hr., 20 min. bake at 260° C.
[2]Prepolymer with an average molecular weight of 700 or greater as employed in Examples 2, 3 and 4.
[3]A mixture of predominantly monofunctional formaldehyde-diaromatic ethers as employed in Example 1.
[4]p-Toluene sulfonic acid.
[5]Dodecyl diphenyl oxide disulfonic acid.

TABLE 4

Effect of Cure Cycle

| | | % Wt. Loss After 500 Hrs. at 500° F. | |
|---|---|---|---|
| Catalyst | Prepolymer | 6 Hours | 14 hours |
| — | Doryl ® | 4.72 | 3.56 |
| p-Tol.[1] | Type 1[3] | 5.36 | 3.14 |
| DDODA[2] | Type 1 | 5.74 | 3.54 |
| p-Tol. | Type 2[4] | 3.99 | 2.29 |

TABLE 4-continued

Effect of Cure Cycle

| Catalyst | Prepolymer | % Wt. Loss After 500 Hrs. at 500° F. | |
|---|---|---|---|
| | | 6 Hours | 14 hours |
| DDODA | Type 2 | 4.63 | 3.36 |

[1] p-Toluene sulfonic acid.
[2] Dodecyl diphenyl oxide disulfonic acid.
[3] Prepolymer with an average molecular weight of 700 or greater as employed in Examples 2, 3 and 4.
[4] A mixture of predominantly monofunctional formaldehyde-diaromatic ethers as employed in Example 1.

TABLE 5

Effect of Catalyst Selection

| Prepolymer | Cure Cycle | % Wt. Loss After 500 Hrs. at 500° F. | |
|---|---|---|---|
| | | p-Tol.[1] | DDODA[2] |
| Type 1[3] | 6 Hrs. | 5.36 | 5.74 |
| Type 1 | 14 Hrs. | 3.14 | 3.54 |
| Type 2[4] | 6 Hrs. | 3.99 | 4.63 |
| Type 2 | 14 Hrs. | 2.29 | 3.36 |

[1] p-Toluene sulfonic acid.
[2] Dodecyl diphenyl oxide disulfonic acid.
[3] Prepolymer with an average molecular weight of 700 or greater as employed in Examples 2, 3 and 4.
[4] A mixture of predominantly monofunctional formaldehyde-diaromatic ethers as employed in Example 1.

I claim:

1. A polymer derived by heating, in the presence of an acid catalyst at between about 140° and 165° C., a mixture consisting essentially of one monomeric compound selected from each of two or all four of the following groups
   A. methoxy methyl diphenyl oxide or sulfide or their alkyl or halogenated derivatives;
   B. methoxy poly(methoxy)methyl diphenyl oxide or sulfide or their alkyl or halogenated derivatives;
   C. di[methoxy poly(methoxy)methyl] diphenyl oxide or sulfide or their alkyl or halogenated derivatives;
   D. methoxy methyl poly(phenoxyphenyl methylene) phenoxybenzene, any one of which A to D may contain unreacted diphenyl oxide or sulfide and bis(phenoxy phenyl) methane,
   said compounds falling within the following generic formula

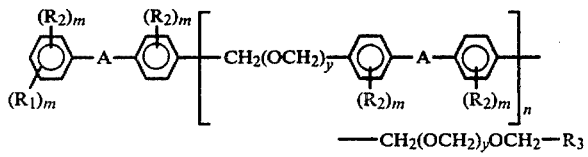
——CH$_2$(OCH$_2$)$_y$OCH$_2$—R$_3$ wherein each A represents a chalcogen independently selected from the group oxygen and sulfur; R$_1$ represents a member selected from the group hydrogen, —CH$_2$(OCH$_2$)$_y$OCH$_2$-R$_3$; each R$_2$ represents a member independently selected from the group consisting of R$_1$, halogen and an alkyl group of 1 to 10 carbon atoms; R$_3$ represents a member selected from the group consisting of H, methyl, ethyl and propyl; each m represents an independently selected integer from 1 to 2; n represents an integer from 0 to 60 and y represents an integer from 0 to 3.

2. A polymer prepared as in claim 1 wherein the acid catalyst is a sulfonic acid.

3. A polymer prepared as in claim 1 wherein the acid catalyst is p-toluene sulfonic acid.

4. A polymer prepared as in claim 1 wherein the acid catalyst is dodecyl diphenyl oxide disulfonic acid.

5. A polymer prepared as in claim 1 wherein the monomeric compounds have an average equivalent weight of about 214.

6. A polymer prepared as in claim 1 wherein the monomeric compounds have an average equivalent weight of about 262.

7. A polymer prepared as in claim 1 wherein the monomeric compounds have an average molecular weight of about 700.

8. A thermoset resin prepared by heating the polymer of claim 1 at 170° to 260° C. for from several minutes to several hours.

9. A thermoset resin prepared by heating the polymer of claim 5 at 170° to 260° C. for from several minutes to several hours.

10. A thermoset resin prepared by heating the polymer of claim 6 at 170° to 260° C. for from several minutes to several hours.

11. A thermoset resin prepared by heating the polymer of claim 7 at 170° to 260° C. for from several minutes to several hours.

12. A polymer derived by heating, in the presence of a catalytic amount of dodecyl diphenyl oxide disulfonic acid at between about 140° and 165° C., a mixture consisting essentially of at least one monomeric compound selected from each of the following groups
   A. methoxy methyl diphenyl oxide or sulfide or their alkyl or halogenated derivatives;
   B. methoxy poly(methoxy)methyl diphenyl oxide or sulfide or their alkyl or halogenated derivatives;
   C. di[methoxy poly(methoxy)methyl] diphenyl oxide or sulfide or their alkyl or halogenated derivatives;
   D. methoxy methyl poly(phenoxyphenyl methylene) phenoxybenzene, any one of which A to D may contain unreacted diphenyl oxide or sulfide
   said compounds falling within the following generic formula:

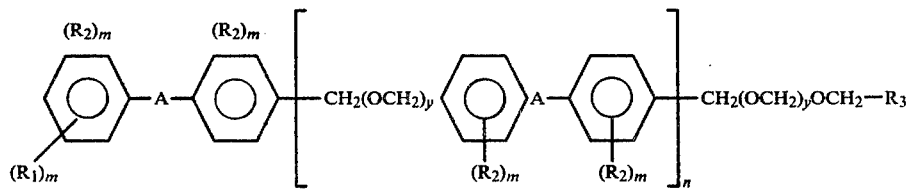

wherein each A represents a chalcogen independently selected from the group oxygen and sulfur; R$_1$ represents a member selected from the group hydrogen, —CH$_2$(OCH$_2$)$_y$ OCH$_2$—R$_3$; each R$_2$ represents a member independently selected from the group consisting of R$_1$; halogen and an alkyl group of 1 to 10 carbon atoms; R$_3$ represents a member selected from the group consisting of H, methyl, ethyl and propyl; each m represents an independently selected integer from 1 to 2; n represents an integer from 0 to 60 and y represents an integer from 0 to 3.

* * * * *